United States Patent [19]

Marais et al.

[11] 4,316,461
[45] Feb. 23, 1982

[54] INTRAVENOUS VASCULAR STABILIZER

[76] Inventors: Henri J. Marais, 218 South St., Waltham, Mass. 02154; Kevin M. Morrison, 320 Lynnfield St., Lynn, Mass. 01904

[21] Appl. No.: 123,893

[22] Filed: Feb. 22, 1980

Related U.S. Application Data

[63] Continuation-in-part of Ser. No. 770,684, Feb. 22, 1977, abandoned.

[51] Int. Cl.³ ............................................... A61M 5/00
[52] U.S. Cl. .............................. 128/214 R; 128/133; 128/DIG. 26; 128/327
[58] Field of Search .................... 128/133, 214 R, 215, 128/221, 327, DIG. 26

[56] References Cited

U.S. PATENT DOCUMENTS

| 1,824,516 | 9/1931 | Tyvand | 128/327 |
| 2,008,340 | 7/1935 | Salvati et al. | 128/215 |
| 3,900,026 | 8/1975 | Wagner | 128/133 |

FOREIGN PATENT DOCUMENTS

| 1003251 | 11/1951 | France | 128/133 |

*Primary Examiner*—Dalton L. Truluck
*Attorney, Agent, or Firm*—Barlow & Barlow

[57] ABSTRACT

This invention provides a vascular stabilizer in which a base plate that has a major medial longitudinal aperture or slot is adapted to be positioned so that the edges of the slot embrace a vein. The slot is defined by an arched connector or hood portion to rigify the slot and to protect a needle-type catheter in inserted position and means are provided to readily secure the base plate member to the patient as well as exerting mild pressure on either side of the vein to be infused.

7 Claims, 9 Drawing Figures

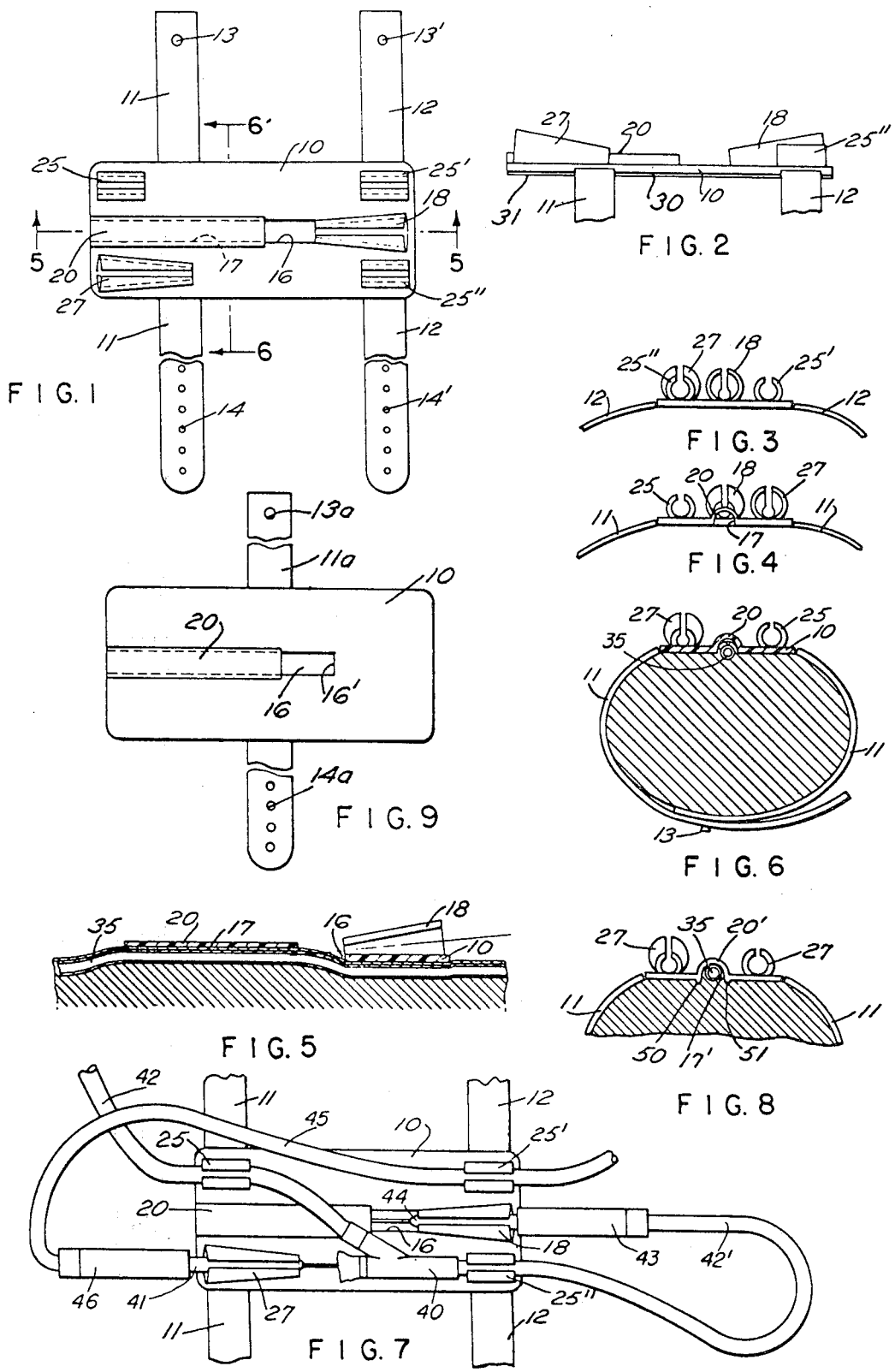

INTRAVENOUS VASCULAR STABILIZER

CROSS REFERENCE TO RELATED APPLICATIONS

This application is a continuation-in-part of our applications Ser. No. 770,684 filed Feb. 22, 1977, and Ser. No. 939,433 filed Sept. 5, 1978, now abandoned.

BACKGROUND OF THE INVENTION

Catheters are widely used for introducing fluids into the body in intravenous therapy and in transferring medicinal fluids. This type of catheter utilizes a puncturing element as the fluid passage portion and an enlarged means on the needle shaft to connect sterile fluid tubing thereto. In devices of this nature the results are not always completely satisfactory as there is a tendency of the puncturing element, that is the needle, to dislocate itself. As a result there are great swathes of surgical adhesive tape binding down the intravenous devices to the limbs of the unfortunates who need them. There are even greater problems in the anchoring of additional or so-called piggyback infusion units which again require more taping of the Y connections and the sterile tubing that connect to the catheters.

Heretofore, devices such as wing structures and tape have been employed to fix the catheter in place on the limb after vena puncture has taken place. Common forms of wing structures are shown in U.S. Pat. Nos. 3,064,648; 3,074,984 and 3,782,383, the latter utilizing two wing portions. It also has been suggested to provide a holder and protection hood for intravenous needles such as is illustrated in U.S. Pat. No. 3,900,026. Even this approach has a deficiency in that it lacks a fast, safe way of needle removal and disposal by effectively stabilizing the vein. A stabilizing support as disclosed in French Pat. No. 1,003,251 suggests a straight plate stabilizer but does not provide the rigidfication of the stabilizing slot enabling the same to elevate the vascular member.

SUMMARY OF THE INVENTION

According to the present invention there is an improved device for catheters or other devices for vascular infusion which stabilizes the vein and may also grip the catheter. The device basically comprises a base plate that is preferably formed with an integral strap means extending therefrom to have a simple locking means thereon and a small, simple disposable transparent flexible unit that can be readily sterilized and maintained in a sterile package. The plate may be provided with a self-adhering adhesive on the underside thereof. In one form of the invention, the base plate may be provided with a number of clips to accommodate infusion tubing, Y connectors and the like.

The invention provides a vascular stabilizer that comprises a semi-rigid right-angular plate that has a central slot or aperture therein which slot, and more particularly the side edges thereof, serves as a stabilizing means for the vein so that the vein will be noticeably elevated as well as laterally stabilized. The central slot is partially defined by edges that are joined by an arched connector portion particularly over the portion of the vascular strand into which the needle is inserted to provide a pressure point to protect the needle when inserted as well as maintaining a visual contact with the area being punctured. At one end of the slot, a fastener means into which the needle or catheter may be fitted may be provided.

Accordingly, the invention has for its primary purpose the provision of a device to simplify a somewhat difficult procedure using needle-type catheters in a safe and comfortable manner.

Still a further object of the invention is to provide a device which will localize, elevate and stabilize vascular structures during and after intravenous infusion.

DESCRIPTION OF THE DRAWINGS

FIG. 1 is a top plan view illustrating the vascular stabilizer of this invention;

FIG. 2 is a side view of the structure illustrated in FIG. 1;

FIG. 3 is an end view taken from the righthand side of FIG. 1;

FIG. 4 is an end view taken from the lefthand side of FIG. 1;

FIG. 5 is a central sectional view taken on lines 5—5 of FIG. 1;

FIG. 6 is a view taken substantially on lines 6—6 of FIG. 1 with the device in place on a limb;

FIG. 7 is a plan view of the stabilizer with auxiliary infusions;

FIG. 8 is a sectional view similar to FIG. 6 showing a modified form of stabilizer;

FIG. 9 is a top plan view showing a basic form of stabilizer in accordance with this invention.

DESCRIPTION OF THE PREFERRED EMBODIMENT

Referring to the drawing and particularly FIGS. 1 and 9, the stabilizer comprises a rectangular base plate 10 to which are preferably molded an integral strap 11a or straps 11 and 12 which straps may be provided with a protruding button such as 13a, 13, 13' respectively at one end, while the other end is provided with a plurality of apertures 14a, 14, 14' respectively. It, of course, will be understood that other means of fastening may be employed. The plate 10 has a medial longitudinal aperture or slot 16 therein, which terminates at 16', and the substantial or major portion thereof is provided with an arched hood or bubble-like structure 20 thereover which connects the free edges 17 of the aperture 16 (see FIG. 4). The top surface of the base plate member may be provided with an open bracket or clip or frictional sleeve fastening means 18 and a plurality of infusion tubing stabilizers in the form of clips or semi-circular flexible members designated 25, 25' and 25" and may also be provided with a secondary hub stabilizer 27 also in the form of a flexible clip which is tapered to accommodate the conical form normally found in catheter devices. Further, the bottom surface of the base plate member may have adhesive material 30 thereon suitably protected by a strippable paper cover 31 (see FIG. 2).

To use the device of this invention, the patient is examined by the person who is to administer the intravascular procedure to find the most favorable limb and vessel for the infusion. Standard procedure, then, is to apply a tourniquet and the vessel is reappraised and the area is rendered as sterile as feasible. The stabilizing device of the instant invention which is preferably kept in a sterile package is then removed, and the strippable paper 31 over the adhesive is removed, and the base plate is placed over the prepared area insuring that the chosen vein is fitting firmly in the central slot with the proposed point of insertion being within the arched connector portion or bubble hood area. By exerting pressure on this connector portion or hood, the base plate is pressed downwardly on either side of the vein 35 which is now noticeably elevated into the slot area (see FIG. 5) as well as being laterally stabilized. This step, in and of itself, negates the much maligned lateral motion that complicates normal puncture procedures. Vascular puncture is then effected through the cutaway section of the central slot between the end of the hood and the end of the slot at 16' and once a satisfactory blood return is achieved the catheter is advanced or the needle is advanced carefully and then fastened in place by the use of adhesive tape. In the form shown in FIG. 1, the needle is advanced until its hub is directly over the fastening means 18 and the hub of the catheter is then firmly depressed into the fastening means 18 and the tourniquet is released. In the event of a faulty vascular puncture, the pressure exerted on either side of the vein by the base plate 10 inhibits extensive lateral subcutaneous extension of the infusion fluid. Also if the vessel is damaged and hemorrhage ensues, the pressure afforded by the device on either side of the vein tends to reduce the hemorrhaging extent and inasmuch as the stabilizer body is transparent, any hemorrhage is immediately evident.

It should be recognized that the hood 20 contacts the vein and for the most part prevents hemorrhaging as the hood will exert a pressure downward. Even if the vessel should rupture, the hood 20 will exert the necessary downward pressure and impede an otherwise difficult situation, enabling the operator to control the hemorrhaging.

As will be apparent from examining FIG. 7 of the drawings, additional infusions may readily be effected by providing a Y connection 40 and a secondary catheter 41. Primary tubing 42 leads to the Y connector 40 and thence to tubing 42' with male connector 43 that couples to primary catheter 44. The secondary drug tubing 45 connects with male connector 46 to secondary catheter 41. All the tubing and secondary catheter structure is well supported by clips 25, 25', 25" and hub stabilizer 27.

Referring to FIG. 8 of the drawings, a modified form of the stabilizer is shown where along the portion where the hood 20 extends at the open end 17' there are provided downwardly extending ridges 50 and 51. These ridges 50 and 51 will exert additional pressure on either side of the vascular member and assist in the elevation of the same into the hood 20'.

We claim:

1. An intravenous vascular stabilizer comprising a substantially rigid rectangular base plate having a substantially medial longitudinal aperture defined by edges that closely embrace a vascular strand with an open bracket means terminating one end thereof and a substantially rigid elongated, inverted U-shaped bubble hood means overlying the other end thereof, said hood means having junction means along the sides thereof connecting the edges of said aperture along a substantial length thereof to rigidfy the edges of the longitudinal aperture whereby the open bracket means will snugly hold an intravenous needle collar and the bubble hood will cover a portion of the needle and vasculature and will engage the raised vein when pressed from above.

2. An intravenous vascular stabilizer as in claim 1 wherein the open bracket means is formed with a taper to frictionally grasp the tapered collar portion of the needle and is oriented at an acute angle to the planar extent of the base.

3. An intravenous vascular stabilizer as in claim 1 wherein the base has affixed thereto a plurality of clip means for fastening intravenous tubing.

4. An intravenous vascular stabilizer as in claim 1 wherein flexible strap members extend laterally from the base to encircle a limb.

5. An intravenous vascular stabilizer as in claim 1 wherein the edges of said aperture at the junction with said hood means are provided with downwardly extending ribs.

6. An intravenous vascular stabilizer as in claim 1 wherein the base plate and hood are transparent.

7. An intravenous vascular stabilizer comprising a substantially rigid rectangular base plate having a substantially medial longitudinal aperture defined by edges that closely embrace a vascular strand with an open bracket substantially rigid inverted U-shape bubble hood means overlying substantially the entire length of said aperture, the sides of said hood means connected to the edges of said aperture along a major length thereof to rigify the edges of the longitudinal aperture whereby the bubble hood will cover a substantial portion of the longitudinal aperture and the edges of the longitudinal aperture will engage the raised vein when pressed from above.

* * * * *